US011596758B2

(12) United States Patent
Landis et al.

(10) Patent No.: US 11,596,758 B2
(45) Date of Patent: Mar. 7, 2023

(54) NASAL CANNULA

(71) Applicant: ResMed Pty Ltd, Bella Vista (AU)

(72) Inventors: Robert M. Landis, Mountainside, NJ (US); Charles A. Lewis, Carrabelle, FL (US); Louis Javier Collazo, Lauderdale by the Sea, FL (US)

(73) Assignee: ResMed Pty Ltd

( * ) Notice: Subject to any disclaimer, the term of this patent is extended or adjusted under 35 U.S.C. 154(b) by 0 days.

(21) Appl. No.: 17/387,592

(22) Filed: Jul. 28, 2021

(65) Prior Publication Data

US 2021/0353893 A1 Nov. 18, 2021

Related U.S. Application Data

(63) Continuation of application No. 16/894,453, filed on Jun. 5, 2020, which is a continuation of application (Continued)

(51) Int. Cl.
*A61M 16/06* (2006.01)
*A61M 16/00* (2006.01)
*A61M 16/10* (2006.01)

(52) U.S. Cl.
CPC .... *A61M 16/0672* (2014.02); *A61M 16/0003* (2014.02); *A61M 16/0666* (2013.01); (Continued)

(58) Field of Classification Search
CPC .............. A61M 16/00; A61M 16/0003; A61M 16/0051; A61M 16/0063; A61M 16/021; (Continued)

(56) References Cited

U.S. PATENT DOCUMENTS

| 4,054,133 A | 10/1977 | Myers |
| 4,282,869 A | 8/1981 | Zidulka |
| 4,535,767 A * | 8/1985 | Tiep ................... A61M 16/0666 128/207.18 |

(Continued)

FOREIGN PATENT DOCUMENTS

| DE | 3708146 | 9/1988 |
| FR | 2827778 | 1/2003 |
| WO | WO 2004/105846 | 12/2004 |

OTHER PUBLICATIONS

International Search Report from PCT/US2006/035947, dated Jan. 10, 2007, 5 pages.

*Primary Examiner* — Annette Dixon
(74) *Attorney, Agent, or Firm* — Fish & Richardson P.C.

(57) ABSTRACT

A gas delivery conduit adapted for fluidly connecting to a respiratory gases delivery system in a high flow therapy system. In one embodiment, a nasal cannula includes a base portion defining a first therapeutic gas passageway, a nozzle disposed adjacent the base portion and defining a second therapeutic gas passageway, the first passageway being in gaseous communication with the second passageway and a conduit configured to facilitate sensing that has an inlet side that is independent of and axially spaced apart from an outlet side of the nozzle. The conduit inlet side can extend beyond the nozzle outlet side of the nasal cannula. Additionally, the nasal cannula has a feature adapted to prevent one of the conduit and the nozzle from creating a seal with a user's rare and a feature adapted to prevent one of the conduit and the nozzle from creating a seal with a user's nare.

20 Claims, 16 Drawing Sheets

Related U.S. Application Data

No. 14/266,659, filed on Apr. 30, 2014, now Pat. No. 10,675,427, which is a continuation of application No. 11/520,490, filed on Sep. 12, 2006, now abandoned.

(60) Provisional application No. 60/716,776, filed on Sep. 12, 2005.

(52) U.S. Cl.
CPC . *A61M 16/0677* (2014.02); *A61M 2016/1025* (2013.01); *A61M 2205/18* (2013.01); *A61M 2205/3331* (2013.01); *A61M 2205/3368* (2013.01); *A61M 2205/3379* (2013.01); *A61M 2230/42* (2013.01); *A61M 2230/432* (2013.01)

(58) Field of Classification Search
CPC ............ A61M 16/024; A61M 16/0666; A61M 16/0672; A61M 16/0677; A61M 16/0694; A61M 16/085; A61M 16/0858; A61M 16/127; A61M 2016/0021; A61M 2016/0027; A61M 2016/1025; A61M 2205/18; A61M 2205/3331; A61M 2205/3368; A61M 2205/3379; A61M 2210/0618; A61M 2230/005; A61M 2230/42; A61M 2230/432
See application file for complete search history.

(56) References Cited

U.S. PATENT DOCUMENTS

| | | | | |
|---|---|---|---|---|
| 4,602,644 | A | 7/1986 | DiBenedetto et al. | |
| 4,753,233 | A | 6/1988 | Grimes | |
| 4,989,599 | A * | 2/1991 | Carter | A61M 16/0666 128/207.18 |
| 5,099,836 | A * | 3/1992 | Rowland | A61M 16/0051 128/207.18 |
| 5,335,656 | A * | 8/1994 | Bowe | A61B 5/097 128/207.18 |
| 5,551,419 | A | 9/1996 | Froehlich et al. | |
| 5,682,881 | A * | 11/1997 | Winthrop | A61M 16/0858 128/911 |
| 6,093,169 | A | 7/2000 | Cardoso | |
| 6,150,661 | A | 11/2000 | McCaul et al. | |
| 6,655,385 | B1 | 12/2003 | Curti et al. | |
| 6,805,126 | B2 | 10/2004 | Dutkiewicz | |
| 7,007,692 | B2 | 3/2006 | Aylsworth et al. | |
| 7,080,645 | B2 * | 7/2006 | Genger | A61M 16/0694 128/204.18 |
| 7,114,497 | B2 | 10/2006 | Aylsworth et al. | |
| 10,675,427 | B2 * | 6/2020 | Landis | A61M 16/0677 |
| 2002/0053346 | A1 | 5/2002 | Curti et al. | |
| 2004/0260161 | A1 | 12/2004 | Melker et al. | |
| 2005/0033247 | A1 * | 2/2005 | Thompson | A61M 16/0666 604/275 |
| 2007/0175473 | A1 | 8/2007 | Lewis et al. | |
| 2008/0051674 | A1 | 2/2008 | Davenport et al. | |
| 2009/0101147 | A1 | 4/2009 | Landis et al. | |

* cited by examiner

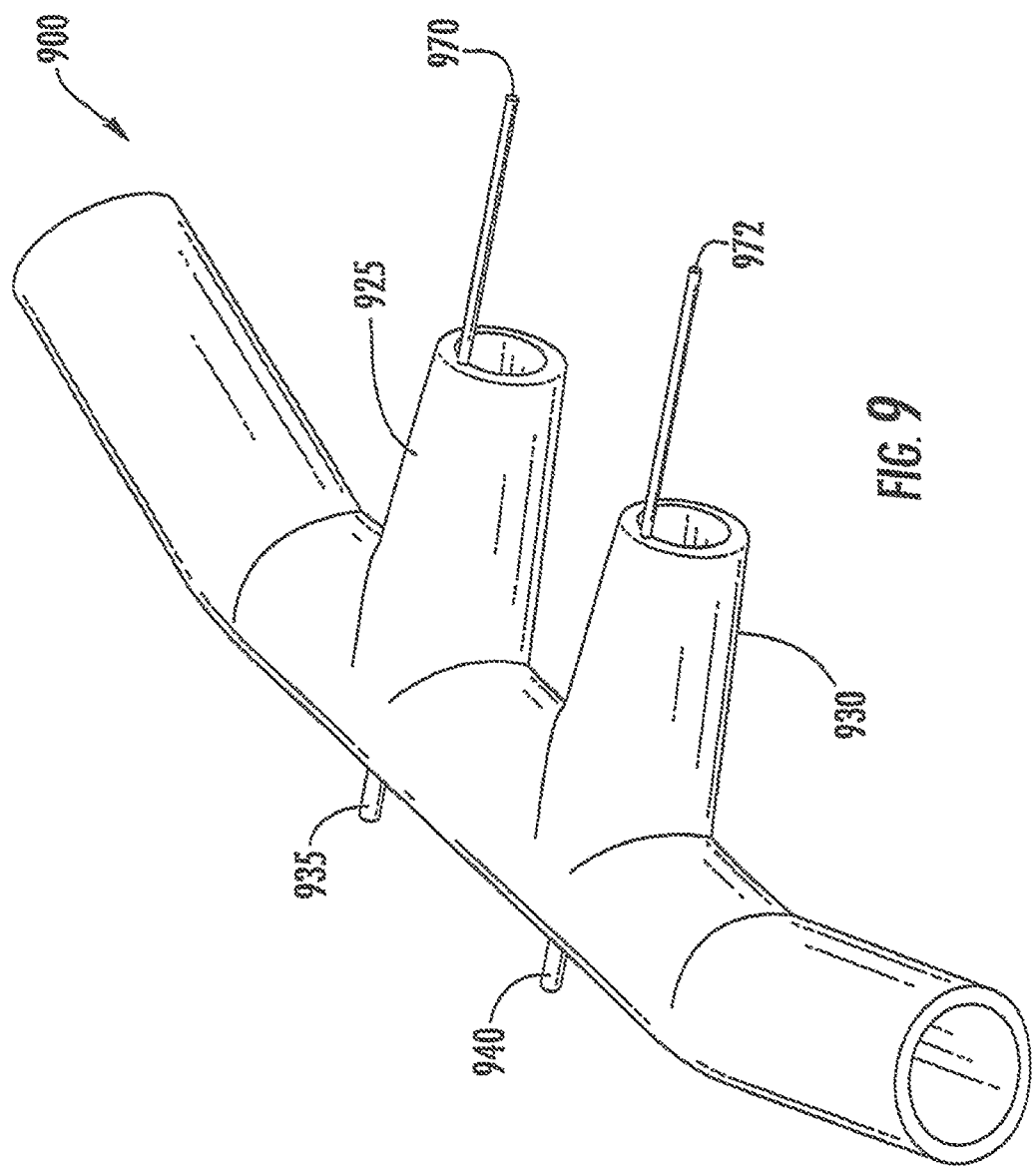

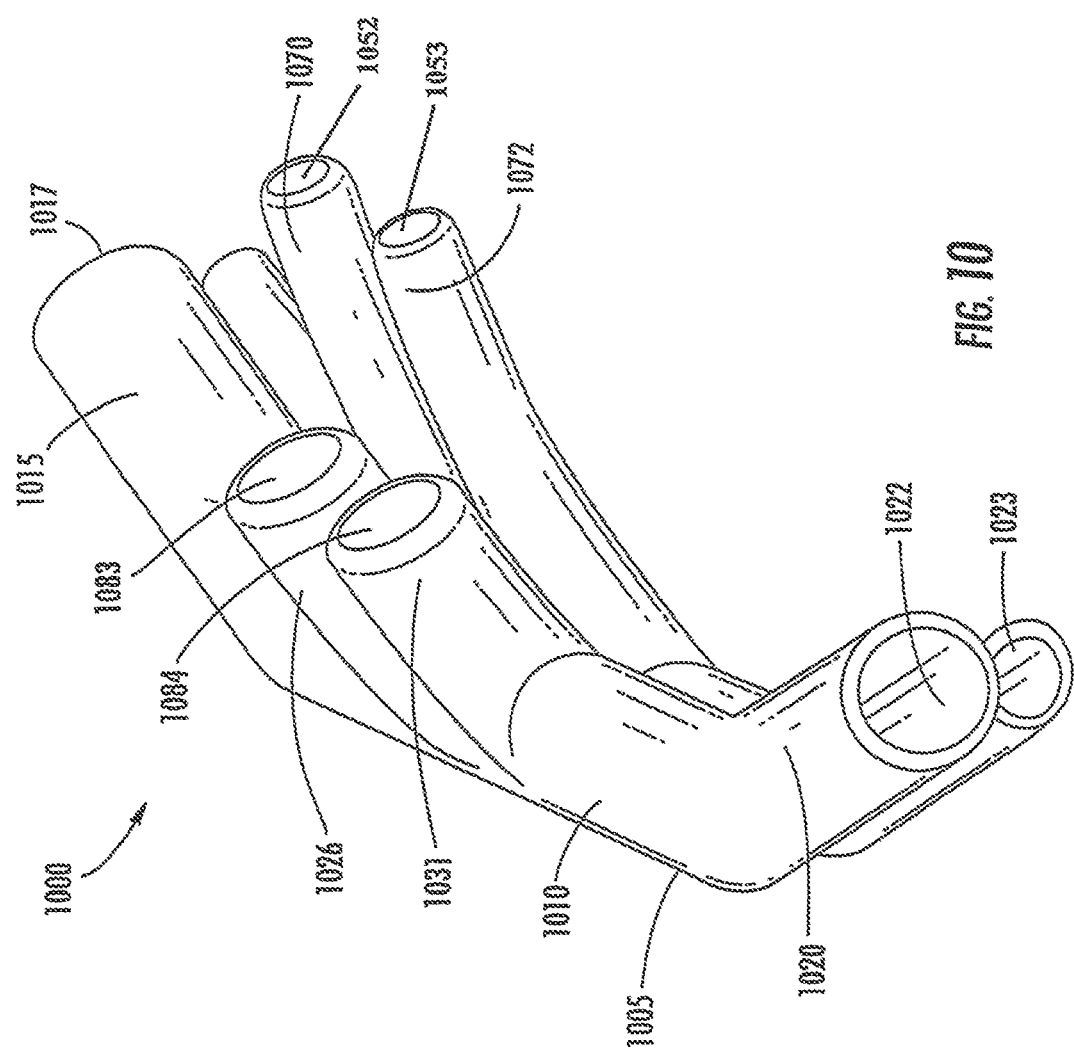

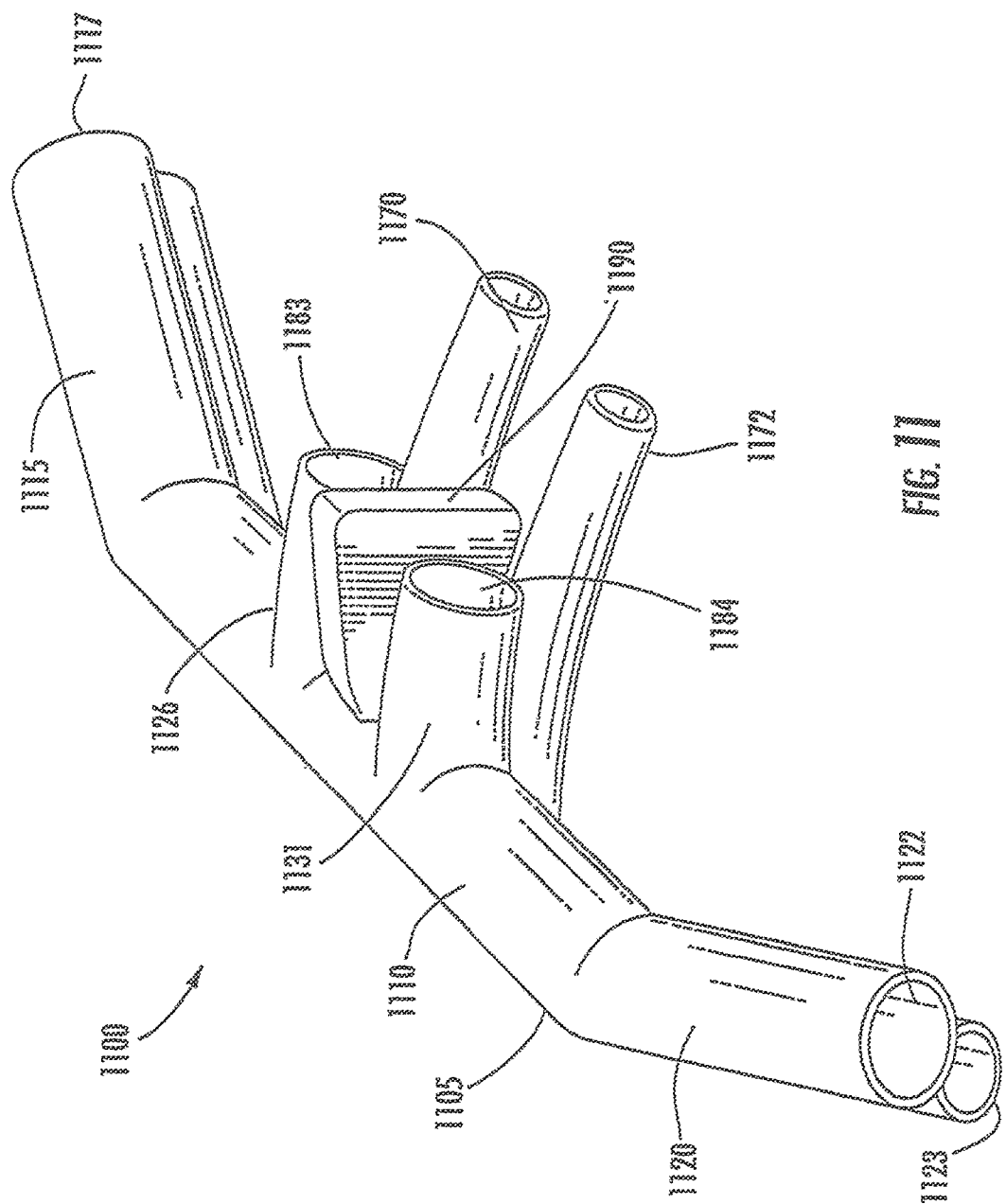

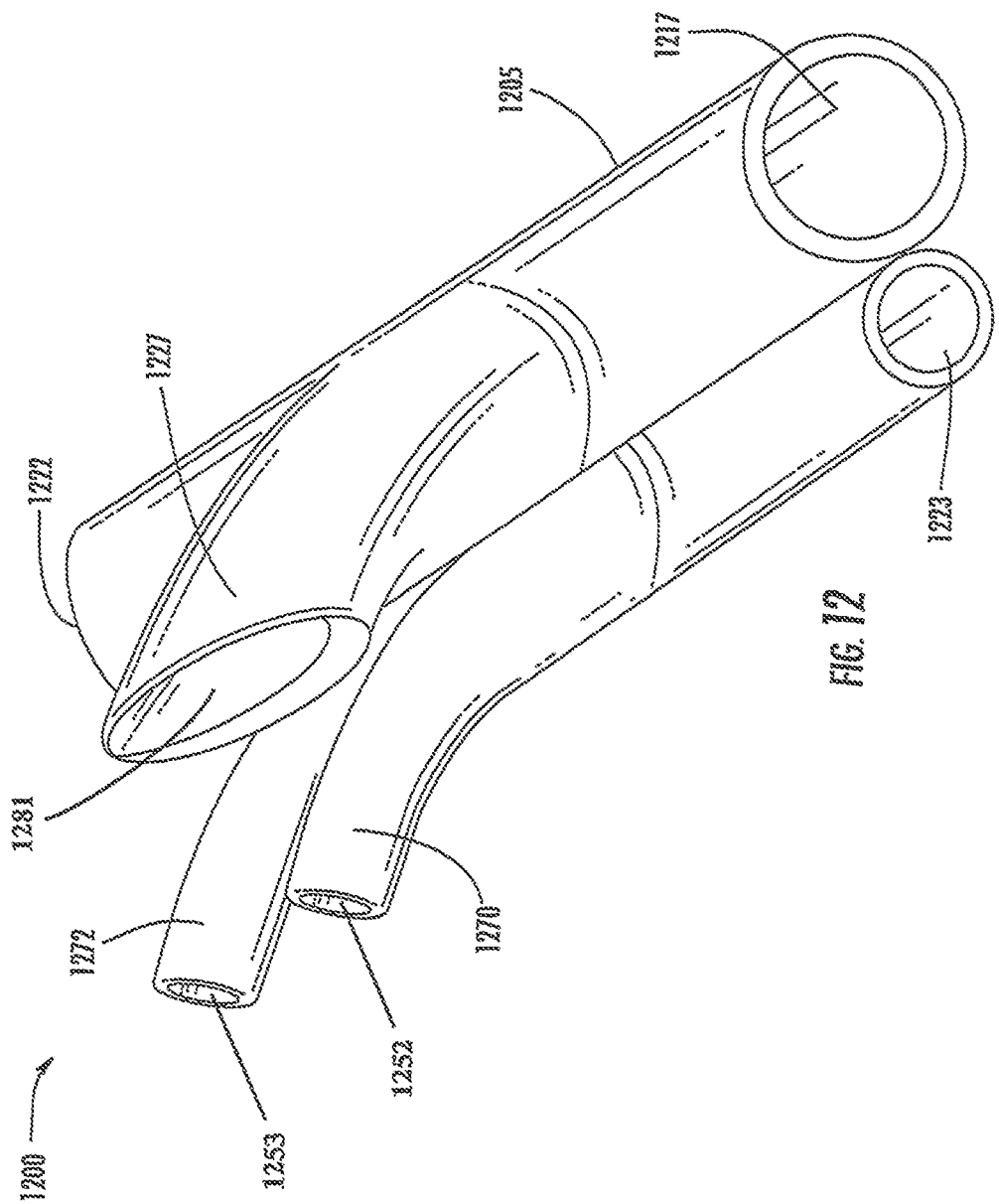

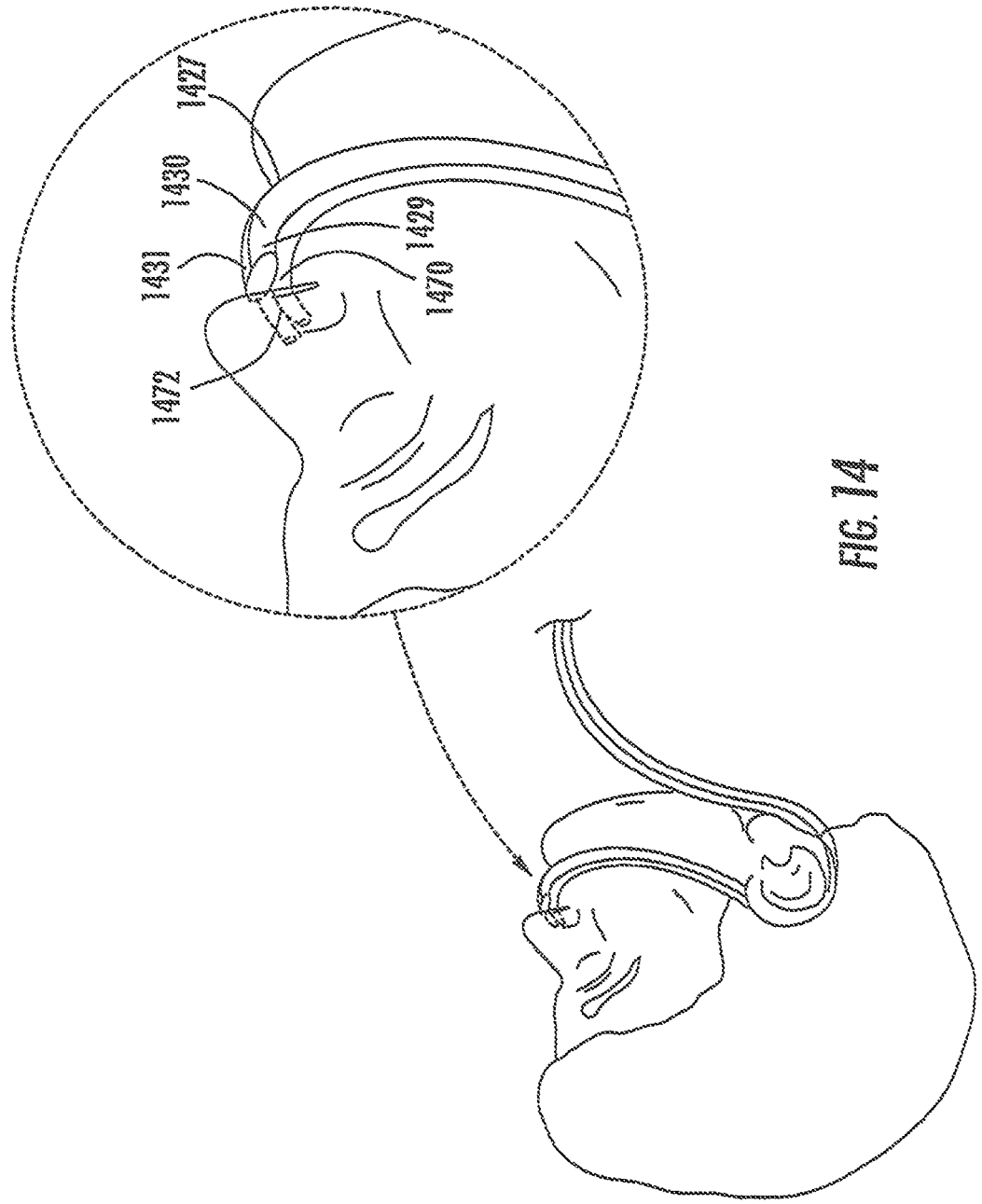

NASAL CANNULA

CROSS-REFERENCE TO RELATED APPLICATIONS

This application is a continuation of U.S. patent application Ser. No. 16/894,453 filed Jun. 5, 2020, which is a continuation of U.S. patent application Ser. No. 14/266,659 filed Apr. 30, 2014, now issued as U.S. Pat. No. 10,675,427 on Jun. 9, 2020, which is a continuation of U.S. patent application Ser. No. 11/520,490 filed Sep. 12, 2006, which claims the benefit of the filing date of U.S. Provisional Patent Application No. 60/716,776 filed Sep. 12, 2005, all of which are incorporated herein by reference.

BACKGROUND

Nasal cannulas are used to deliver respiratory gases for therapeutic effect, including $O_2$ therapy, treatment for sleep apnea, and respiratory support. However, treatment with certain types of nasal cannulas may be limited by the lack of information available on important treatment parameters. These parameters include information regarding the gases within the user's upper airway, such as pressure, flow rate, and carbon dioxide build-up. These and other data may be useful in judging the efficacy of treatment as well as for controlling and monitoring treatment.

In addition, prior art nasal cannula designs (especially those designed for neonatal oxygen therapy) may undesirably create a seal with the user's nares, which may have detrimental effects on the user's health.

SUMMARY

The present disclosure relates to a gas delivery conduit adapted for fluidly connecting to a respiratory gases delivery system in a high flow therapy system. In one embodiment, a nasal cannula includes a base portion defining a first therapeutic gas passageway, a nozzle disposed adjacent said base portion and defining a second therapeutic gas passageway, the first therapeutic gas passageway being in gaseous communication with the second therapeutic gas passageway and a conduit configured to facilitate sensing that has an inlet side that is independent of and axially spaced apart from an outlet side of the nozzle. In one aspect of this embodiment, the conduit inlet side extends beyond said nozzle outlet side of the nasal cannula. In another aspect of this embodiment, the nasal cannula has a feature that is adapted to prevent one of the conduit and the nozzle from creating a seal with a user's nare. In another aspect of this embodiment, the nasal cannula has a feature that is adapted to prevent one of the conduit and the nozzle from creating a seal with a user's nare.

BRIEF DESCRIPTION OF THE DRAWINGS

Reference will now be made to the accompanying drawing figures, which are not necessarily drawn to scale.

FIG. 9 is a perspective view of a nasal cannula according to a further embodiment of the invention.

FIG. 10 is a perspective view of a nasal cannula according to another embodiment of the invention.

FIG. 11 is a perspective view of a nasal cannula according to a further embodiment of the invention.

FIG. 12 is a perspective view of a nasal cannula according to yet another embodiment of the invention.

FIG. 14 illustrates another embodiment of a nasal cannula in use on a patient, according to a further embodiment of the invention.

DETAILED DESCRIPTION OF THE INVENTION

Figure 1:
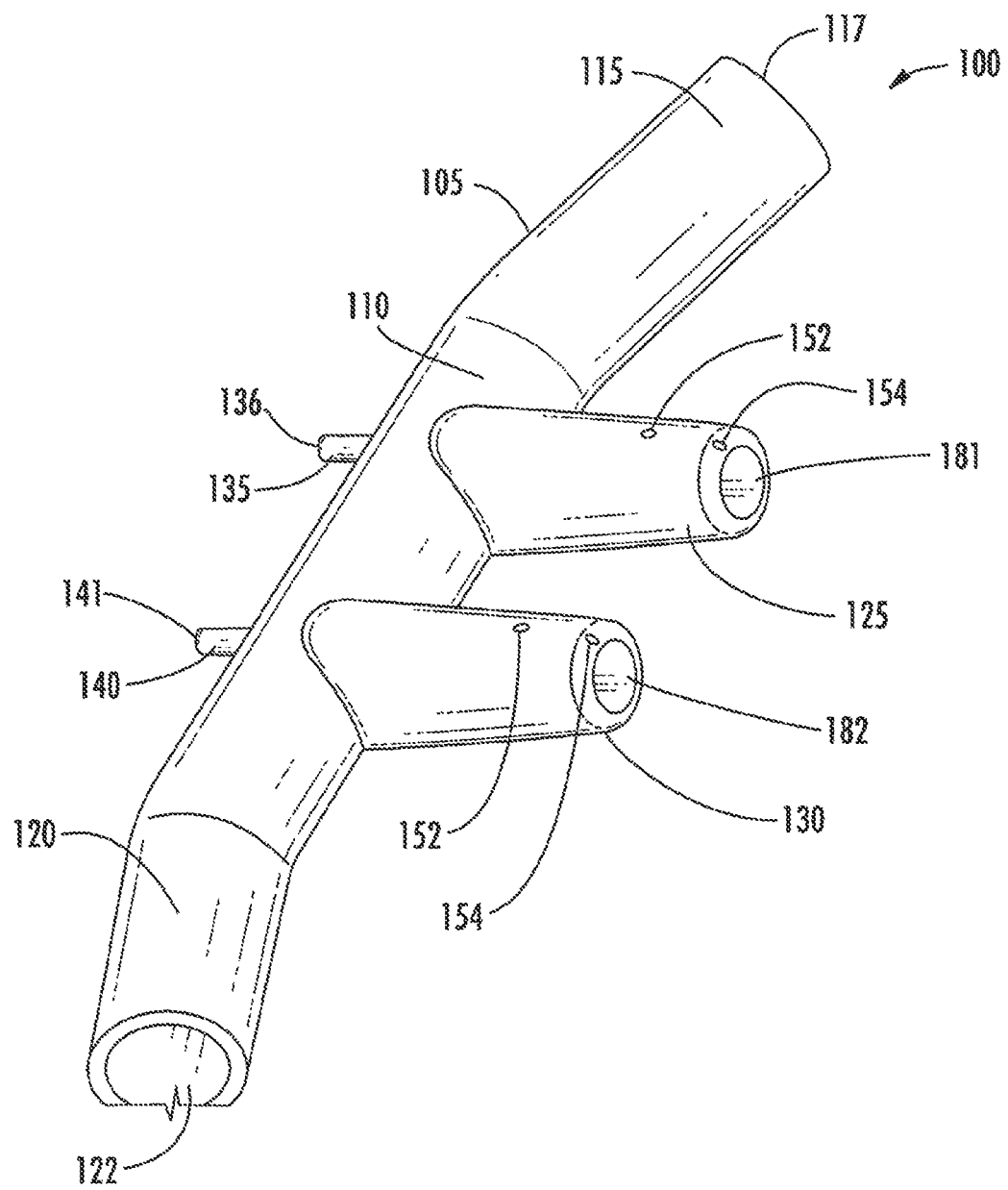
FIG. 1 is a perspective view of a nasal cannula according to a particular embodiment of the invention.

The present inventions now will be described with reference to the accompanying drawings, in which some, but not all embodiments of the inventions are shown. Indeed, these inventions may be embodied in many different forms and should not be construed as limited to the embodiments set forth herein. Rather, these embodiments are provided so that this disclosure will satisfy applicable legal requirements. Like numbers refer to like elements throughout. For example, elements 130, 230, 330, 430, 530, 830, and 930 are all nozzles according to various embodiments of the invention.

Overview of Functionality

Nasal cannula according to various embodiments of the invention may be configured to deliver high-flow therapeutic gases to a patient's upper airway through the patient's nose. Such gases may include, for example, air, humidity, oxygen, therapeutic gases or a mixture of these, and may be heated or unheated. In particular embodiments of the invention, the cannula may be useful for CPAP (continuous positive airway pressure) applications, which may be useful in the treatment of sleep apnea and in providing respiratory support to patients (e.g., after abdominal surgery), to alleviate snoring, or for other therapeutic uses.

Nasal cannula according to particular embodiments of the invention include (or are adapted to facilitate the positioning of) one or more sensors adjacent or within one or more of the cannula's nasal inserts. Accordingly, the nasal cannula may be configured so that at least a portion of one or more sensors is in place in one or both of a user's nares when the nasal cannula is operably worn by the user. This may be particularly helpful in evaluating the environment of the internal portion of the user's nose and/or the user's upper airway. As described in greater detail below, in various embodiments of the invention, the cannula is adapted so that it will not create a seal with the patient's nares when the cannula is in use.

Nasal cannula according to other embodiments of the invention include nozzles. A nozzle may be a nasal insert that is inserted into the user's nares. Other nozzles are adapted to remain outside of a user's nares while the cannula is in use. Accordingly, the nozzles avoid sealing with the patient's nares while the cannula is in use. In some embodiments, the nasal cannula include elongate extensions that are inserted into the user's nares to detect pressure in one or both nares.

In certain embodiments of the invention, sensors are provided adjacent or within both of the nasal cannula's nozzles. In various other embodiments, sensors are provided adjacent or within one or more elongate extensions that extend into the user's nares. In various embodiments, elongate extensions may be used in conjunction with nasal inserts or with nozzles. The use of sensors may be useful, for example, in monitoring environmental changes from one of the user's nares to the other. This information may be helpful, for example, in determining when the dominant flow of air changes from one of the user's nares to the other, which may affect the desired flow characteristics of therapy. Accordingly, data from each nare may provide information that may be useful in establishing
or modifying the user's treatment regimen. Further, multiple sensors may be used in various embodiments.

Overview of Exemplary Cannula Structures

A cannula 100 according to one embodiment of the invention is shown in FIG. 1. As may be understood from this figure, in this embodiment, the cannula 100, includes a hollow, elongated tubular base portion 105 that includes a central portion 110, a first end portion 115, and a second end portion 120. The first and second end portions 115, 120 may be angled relative to the central portion 110 as shown in FIG. 1.

In various embodiments of the invention, the cannula 100 includes a first tubing inlet 117 adjacent the outer end of the first end portion 115, and a second tubing inlet 122 adjacent the second end portion 120 (in other embodiments, the cannula may include only one such inlet). The cannula 100 further comprises a pair of hollow, elongated, tubular nozzles (e.g., nasal catheters) 125, 130 that extend outwardly from the nasal cannula's base portion 105 and that are in gaseous communication with the base portion's interior. In various embodiments, the respective central axes of the nozzles 125, 130 are substantially parallel to each other, and are substantially perpendicular to the central axis of the central portion 110 of the nasal cannula's base portion 105.

In particular embodiments of the invention, the cannula defines at least one conduit that is adapted to guide at least one sensor so that the sensor is introduced adjacent or into the interior of the cannula so that, when the cannula is being operably worn by a user, the environment being monitored by the at least one sensor reflects that of the internal portion of the user's nose and/or the user's upper airway. In various embodiments of the invention, a user may temporarily insert the at least one sensor into or
through the conduit to determine correct settings for the cannula system, and then may remove the sensor after the correct settings have been achieved. In other embodiments, the at least one sensor may be left in place within the conduit for the purpose of monitoring data within (or adjacent) the cannula over time (e.g., for purposes of controlling the user's therapy regimen). In a further embodiment, the at least one sensor may be positioned adjacent an outlet of the conduit.

The at least one sensor may be connected (e.g., via electrical wires) to a computer and/or a microprocessor that is controlling the flow of respiratory gases into the cannula. The computer may use information received from the at least one sensor to control this flow of gas and/or other properties of the system, or may issue an alarm if the information satisfies pre-determined criteria (e.g., if the information indicates potentially dangerous conditions within the patient's airway or if the system fails to operate correctly).

Figure 8A:
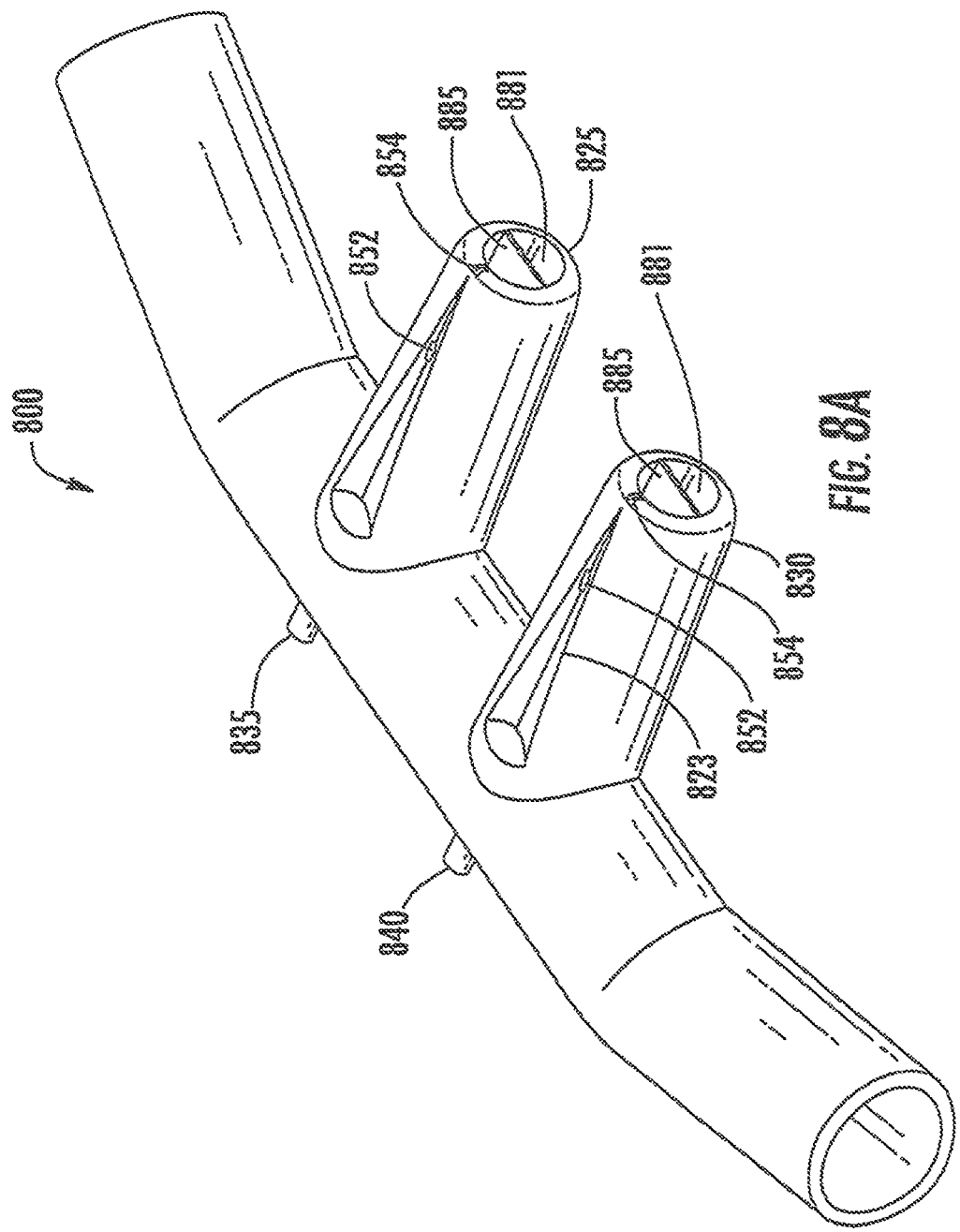
FIG. 8A is a front perspective view of a nasal cannula according to another embodiment of the invention.
Figure 8B:
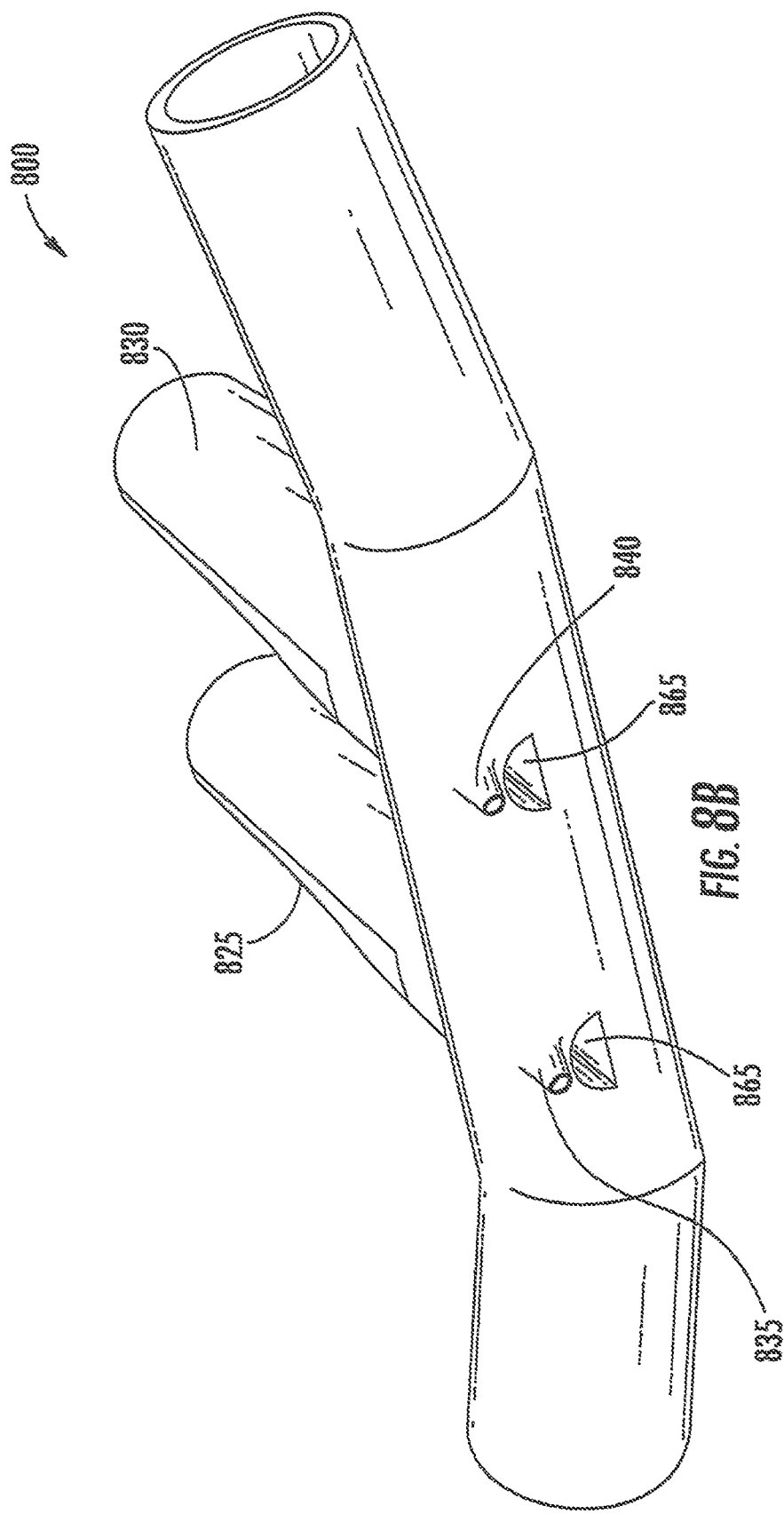
FIG. 8B is a rear perspective view of the nasal cannula shown in FIG. 8A.
Figure 8C:
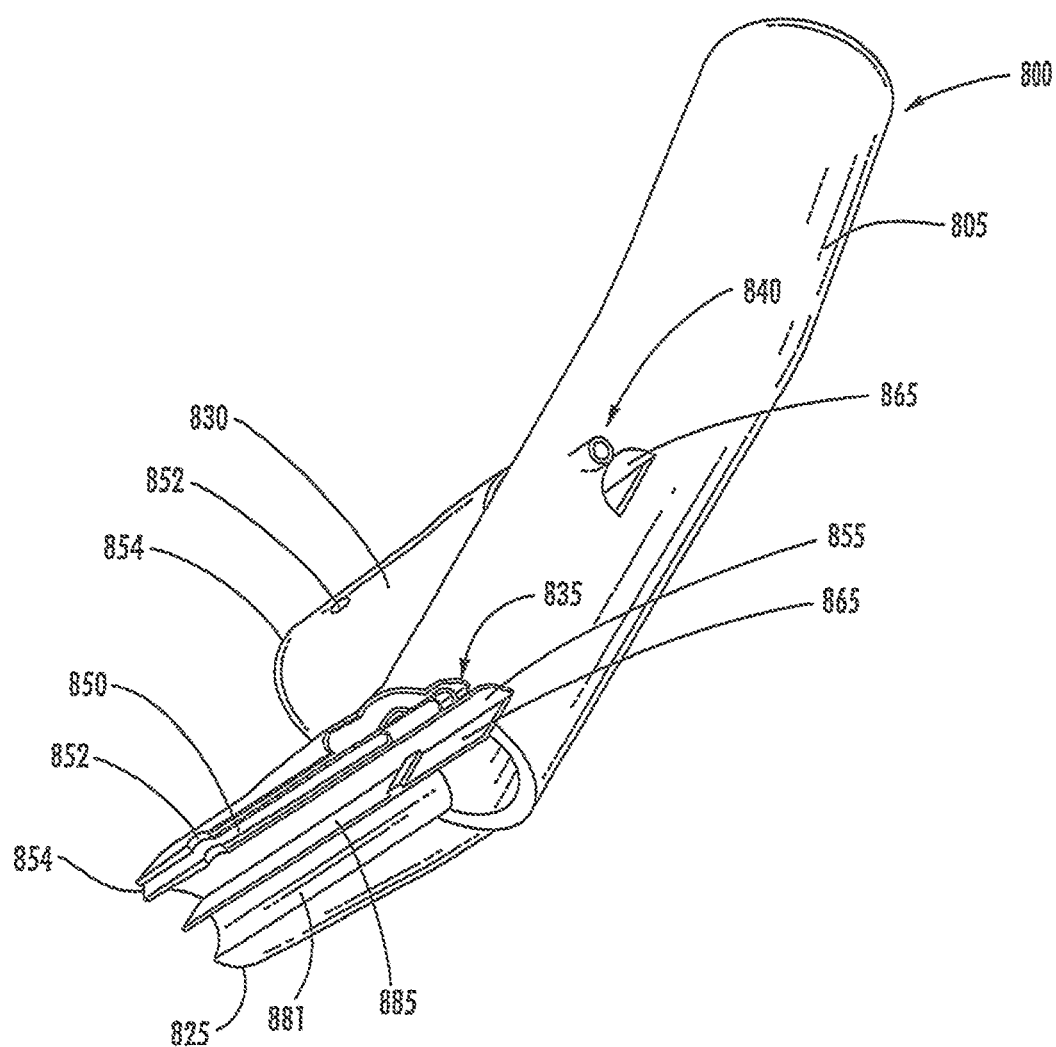
FIG. 8C is a perspective cross-sectional view of the nasal cannula shown in FIG. 8A.

As may be understood from FIGS. 8A-8C, in a particular embodiment of the invention, at least one of the cannulas conduits 850 is defined by, and extends within, a side wall of the cannula 800. Alternatively, the conduit may be disposed within an interior passage defined by the cannula. For example, one or more of the conduits may be defined by a tube that is attached immediately adjacent an interior surface of the cannula (e.g., adjacent an interior surface of the cannula's base portion, or an interior surface of one of the cannulas nozzles). The cannulas conduits are preferably adapted for: (1) receiving a flow of gas at one or more inlets that are in communication with the conduit, and (2) guiding this flow of gas to an outlet in the cannula. In various embodiments, one or more of the inlets is defined within an exterior portion of one of the cannula's nozzles.

As may be understood from FIG. 1, in various embodiments of the invention, each of the cannula's conduit outlets 136, 141 is located
at the end of a respective elongate, substantially tubular, outlet member 135, 140. For example, in the embodiment shown in FIG. 1, the cannula 100 includes a first outlet member 135 that is substantially parallel to the cannula's first nozzle 125. In this embodiment, the first outlet member 135 and the first nozzle 125 may be positioned on opposite sides of the nasal cannula's base portion 105 as shown in FIG. 1. Similarly, in a particular embodiment of the invention, the cannula 100 includes a second outlet member 140 that is substantially parallel to the cannula's second nasal insert 130. The second outlet member 140 and second nozzle 130 are also preferably positioned on opposite sides of the nasal cannula's base portion 105. Nozzles 125, 130 also may have nozzle outlets 181, 182 respectively.

In various embodiments of the invention, a sensor (e.g., a pressure, temperature, or 02 sensor) is provided in communication or adjacent at least one of (and preferably each of) the cannula's outlets 136, 141 and is used to measure the properties of gas from that outlet 136, 141. In a further embodiment of the invention, accessory tubing is used to connect each outlet 135, 140 with at least one corresponding sensor (and/or at least one external monitoring device) that may, for example, be spaced apart from the cannula 100.

In yet another embodiment of the invention, one or more sensors are provided within the conduit, and used to measure the properties of gas accessed through the conduit. In this embodiment, information from each sensor may be relayed to a control system outside the cannula via, for example, an electrical wire that extends from the sensor and through the outlet 135, 140 of the conduit in which the sensor is disposed.

In alternative embodiments of the invention, each of the cannula's conduits may extend: (1) from the conduit inlets 152, 154; (2) through, or adjacent, a side wall of one of the cannula's nozzles 125, 130; (3) through, or
adjacent, a side wall of the cannula's base portion 105; and (4) to an outlet 135, 140 that is defined within, or disposed adjacent, the cannula's base portion 105. In one such embodiment, the conduit comprises a substantially tubular portion that is disposed adjacent an interior surface of the cannula's base portion.

Figure 2:
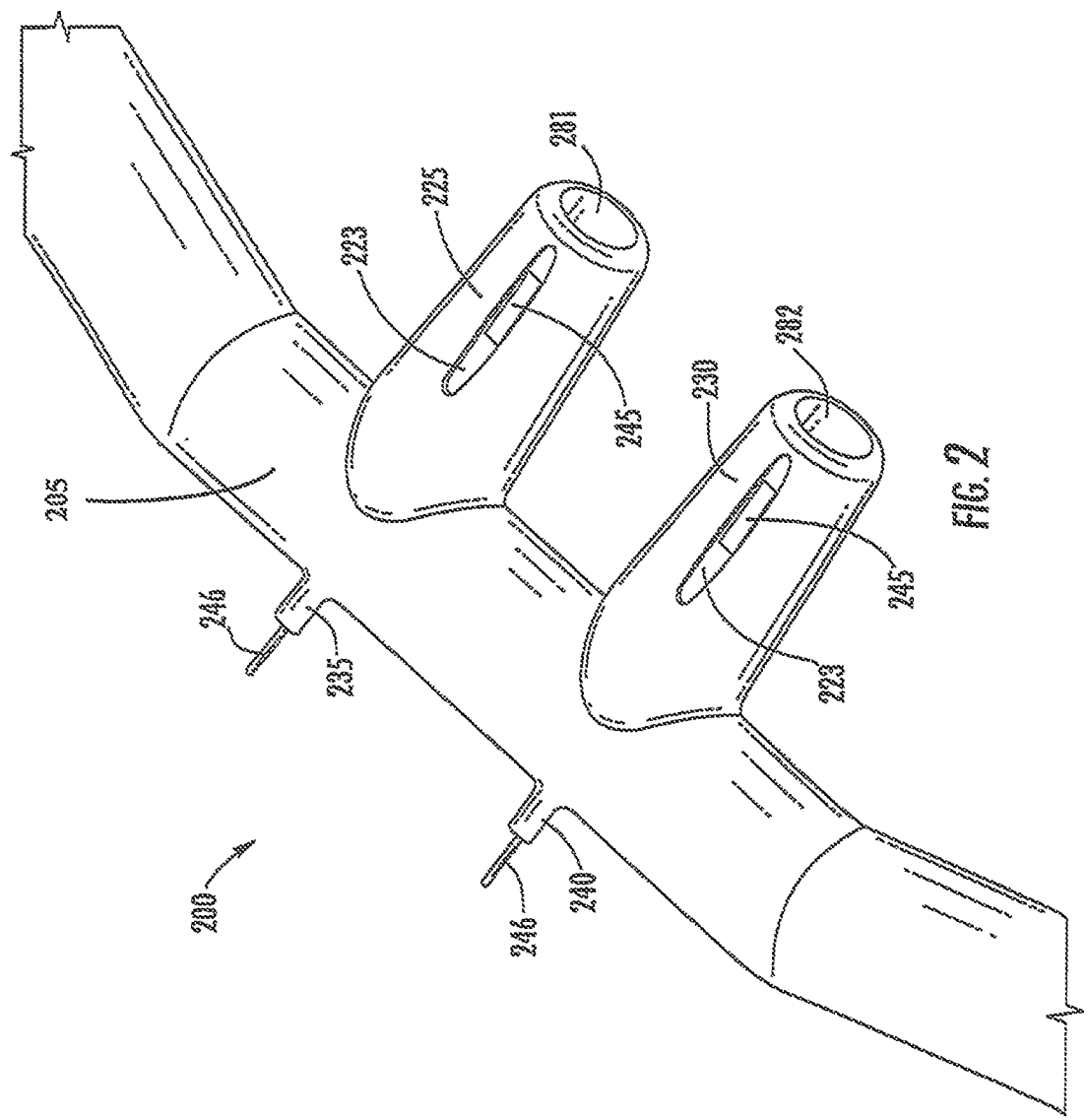
FIG. 2 is a perspective view of a nasal cannula according to a further embodiment of the invention.

As may be understood from FIG. 2, in certain embodiments of the invention, the cannula 200 includes at least one sensor 245 that is integrated into an exterior portion of the cannula 200 (e.g., within a recess 223 formed within an exterior surface of one of the cannula's nozzles 225, 230). In this embodiment, information from the sensor 245 may be relayed to a control system outside the cannula 200 via an electrical wire 246 that extends from the sensor 245, through a conduit, and out an outlet 235, 240 in the conduit. In various embodiments of the invention, the conduit extends through or adjacent an interior portion of a sidewall of one of the cannula's nozzles 225, 230 and/or through or adjacent an interior portion of a sidewall of the cannula's base portion 205. Nozzles 225, 230 also have nozzle outlets 281, 282 respectively.

In particular embodiments of the invention, at least one sensor 245 is fixedly attached to the cannula 100 so that it may not be easily removed by a user. Also, in particular embodiments, at least one sensor 245 is detachably connected adjacent the cannula 100 so that the sensor 245 may be easily detached from (and, in certain embodiments, reattached to) the cannula 100.

The cannula 1000 includes a hollow, elongated tubular base portion 1005 that includes a central portion 1010, a first end portion 1015, and a second end portion 1020. The first and second end portions 1015 and 1020 may be angled relative to the central portion 1010, as shown in FIG. 10. In various embodiments of the invention, the cannula 1000 includes a first tubing inlet 1017 adjacent the outer end of the first end portion 1015, and a second tubing inlet 1022 adjacent the outer end of the second end portion 1020.

The cannula 1000 further comprises a pair of hollow, elongated, tubular nozzles (a first nozzle 1026 and a second nozzle 1031) that extend outwardly from the nasal cannula's base portion 1005. In various embodiments, the respective central axes of the nozzles 1026, 1031 are substantially parallel to each other and are substantially perpendicular to the central axis of the central portion 1010 of the nasal cannula's base portion 1005. In various embodiments, the nozzles 1026, 1031 define passageways that are in gaseous communication with the interior of the cannula's base portion 1005. In particular embodiments of the invention, the first and second nozzles 1026, 1031 are adapted to be positioned outside of a user's nares while the cannula is in use. In particular embodiments, the nozzles 1026, 1031 each define a respective nozzle outlet. For example, the first nozzle 1026 defines a first nozzle outlet 1083, and the second nozzle 1031 defines a second nozzle outlet 1084. In various embodiments, when the nasal cannula 1000 is operatively positioned adjacent a user's nares, each of the nozzle's outlets 1083, 1084 is positioned to direct a focused flow of gas into a corresponding one of the user's nares.

In alternative embodiments, such as the embodiment shown in FIG. 12, the nasal cannula 1200 may include a single nozzle 1227 that defines a passageway that is in gaseous communication with an interior portion of the cannula's base portion 1205. As described in greater detail below, in various embodiments, the nozzle 1227 extends outwardly from the cannula's base portion 1205 and has an oblong, or elliptical, cross-section. In this and other embodiments, the nozzle 1227 is shaped to deliver a focused flow of gas simultaneously into both of a user's nares when the cannula 1200 is in use.

In various embodiments, the nasal cannula includes one or more elongate extensions that are adapted for insertion into one or more of the user's nares. For example, returning to the embodiment shown in FIG. 10, the nasal cannula 1000 may include multiple elongate extensions (for example a first elongate extension 1070 and a second elongate extension 1072) that are long enough to allow each of the elongate extensions 1070, 1702 to be inserted into a respective one of the user's nares while the nasal cannula 1000 is in use. In embodiments, elongate extensions 1070, 1072 may have conduit inlets 1052, 1053 respectively. In various embodiments, each of the elongate extensions 1070, 1072 may have a central axis that runs substantially parallel to the central axis of a corresponding nozzle 1026, 1031. For example, as can be understood from FIG. 10, in certain embodiments, a first elongate extension 1070 has a central axis that lies substantially parallel to and below the central axis of a corresponding first nozzle 1026, when the nasal cannula is operatively positioned adjacent a user's nares. Similarly, in various embodiments, a second elongate extension 1072 has a central axis that lies substantially parallel to and below the central axis of a corresponding second nozzle 1031, when the nasal cannula 1000 is operatively positioned adjacent a user's nares. In various other embodiments, the elongate extensions may lie within, and extend outwardly from, their corresponding nozzles 1070, 1072.

As a further example, FIG. 12 illustrates an exemplary nasal cannula 1200 having multiple elongate extensions (a first elongate extension 1270 and a second elongate extension 1272), which both lie substantially beyond a single nozzle 1227 when the nasal cannula 1200 is in an operative position adjacent the user's nose. In some embodiments, the central axes of the first and second elongate extensions 1270, 1272, may be substantially parallel to the central axis of the nozzle 1227. Also, in various embodiments, one or both of the elongate extensions 1270, 1272 may lie within the nozzle 1227. In this and other embodiments, a distal end of each of the elongate extensions 1270, 1272 may extend beyond a distal end of the nozzle 1227. Elongate extensions 1270, 1272 may have conduit inlets 1252, 1253 respectively, while nozzle 1227 has a nozzle outlet 1281.

As described above, in certain embodiments of the invention, the nasal cannula includes one or more sensors that are adapted to measure gas data (e.g., gas pressure) within the user's nares while the nasal cannula is in use. For example, the nasal cannula 1000 shown in FIG. 10 may include a sensor positioned adjacent the distal end of one or both of the first and second elongate extensions 1070, 1072. In various embodiments, each elongate extension may be adapted to: (1) support a sensor adjacent (e.g., at) the distal end of the elongate extension; and (2) support a wire that is simultaneously connected to the sensor and a control mechanism that is adapted to adjust the properties of gas flowing through the cannula 1000.

In other embodiments, the elongate extensions define conduits. For example, one or more sensor(s) may be positioned within the interior or exterior of the elongate extensions and information from the sensor(s) may be relayed to a control system via a wire extending through a conduit (for example, conduit 1023 of FIG. 10) or passages defined by each of the elongate extensions. In one embodiment, as shown, for example, in FIG. 10, the conduit 1023 is shaped similarly to the nasal cannula's base portion 1005, and lies substantially below the base portion 1005 when the nasal cannula 1000 is operatively in use. In various embodiments, the conduit 1023 is positioned within the base portion 1005 such that the first and second elongate extensions 1070, 1072 lie within, and extend outwardly from, the respective first and second nozzles 1026, 1031.

In various embodiments, each elongate extension defines a respective sensing conduit. For example, in certain embodiments, each sensing conduit is adapted to provide a passage that permits sensing or gaseous communication between a user's nares and a control system or other device for measuring and adjusting the properties of the air. In this and other embodiments, a sensor may be positioned at the control box to measure the properties (e.g., pressure) of air in the user's nares. In some embodiments, the elongate extensions define a conduit that serves both as an air passageway as well as a conduit for allowing a wire to pass from a sensor positioned adjacent the distal tip of the elongate extension to the control system or other device.

Data Monitored by Sensors

In various embodiments of the invention, such as those described above, one or more sensors may be positioned to measure gas data within an interior portion of one of the nasal cannula's conduits, or to measure gas data adjacent an exterior portion of the cannula. In such embodiments, one or more sensors may be, for example, positioned adjacent an interior or exterior surface of the cannula. In certain embodiments of the invention, one or more of the cannula's sensors is adapted to monitor one or more of the following types of data within the cannula's conduits, or adjacent the cannula's exterior surface (e.g., adjacent a side portion, or distal end of, one of the cannula's nozzles): (1) gas pressure; (2) gas flow rate; (3) carbon dioxide content; (4) temperature; (5) level; and/or (6) oxygen content.

Absolute Vs. Relative Pressure Measurements

In various embodiments of the invention, the cannula may be configured for sensing absolute pressure within, or adjacent, a particular portion of the cannula. Similarly, in particular embodiments, the cannula may be configured to measure the difference between the pressure at two different locations within the cannula. This may be done, for example, by providing two separate sensors (e.g., that are positioned in different locations within one of the cannula's conduits), or by providing two physically distinct gas intake conduits, each of which is adapted for routing gas from a different location within the cannula. For example, in various embodiments of the invention shown in FIG. 1, the first conduit inlet 152 may be connected to a first conduit that is adapted for routing gas to a first sensor, and the second conduit inlet 154 may be connected to a physically separate second conduit that is adapted for routing gas to a second pressure sensor. Information from the first and second sensors may then be used to calculate the difference in pressure between the first and second inlets 152, 154. Alternatively, a differential pressure sensor may be used.

Suitable Sensors

Suitable sensors for use with various embodiments of the invention include electronic and optical sensors. For example, suitable sensors may include: (1) Disposable MEM Piezoelectric sensors (e.g., from Silex Microsensors); (2) light-based sensors such as a McCaul $O_2$ sensor—see U.S. Pat. No. 6,150,661 to McCaul; and (3) Micro-pressure sensors, such as those currently available from Honeywell.

Non-Sealing Feature

Figure 3:
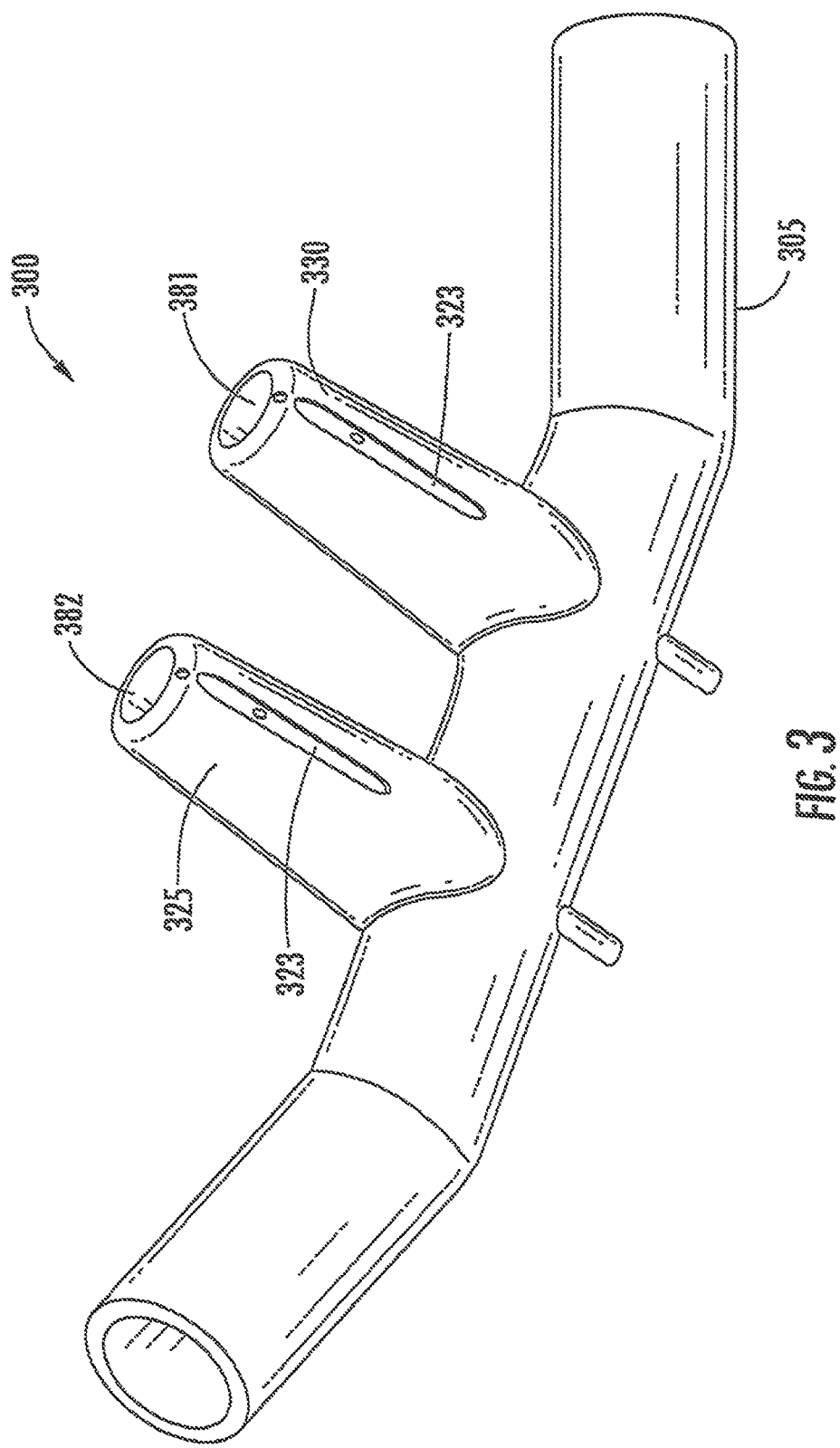
FIG. 3 is a perspective view of a nasal cannula according to another embodiment of the invention.
Figure 4:
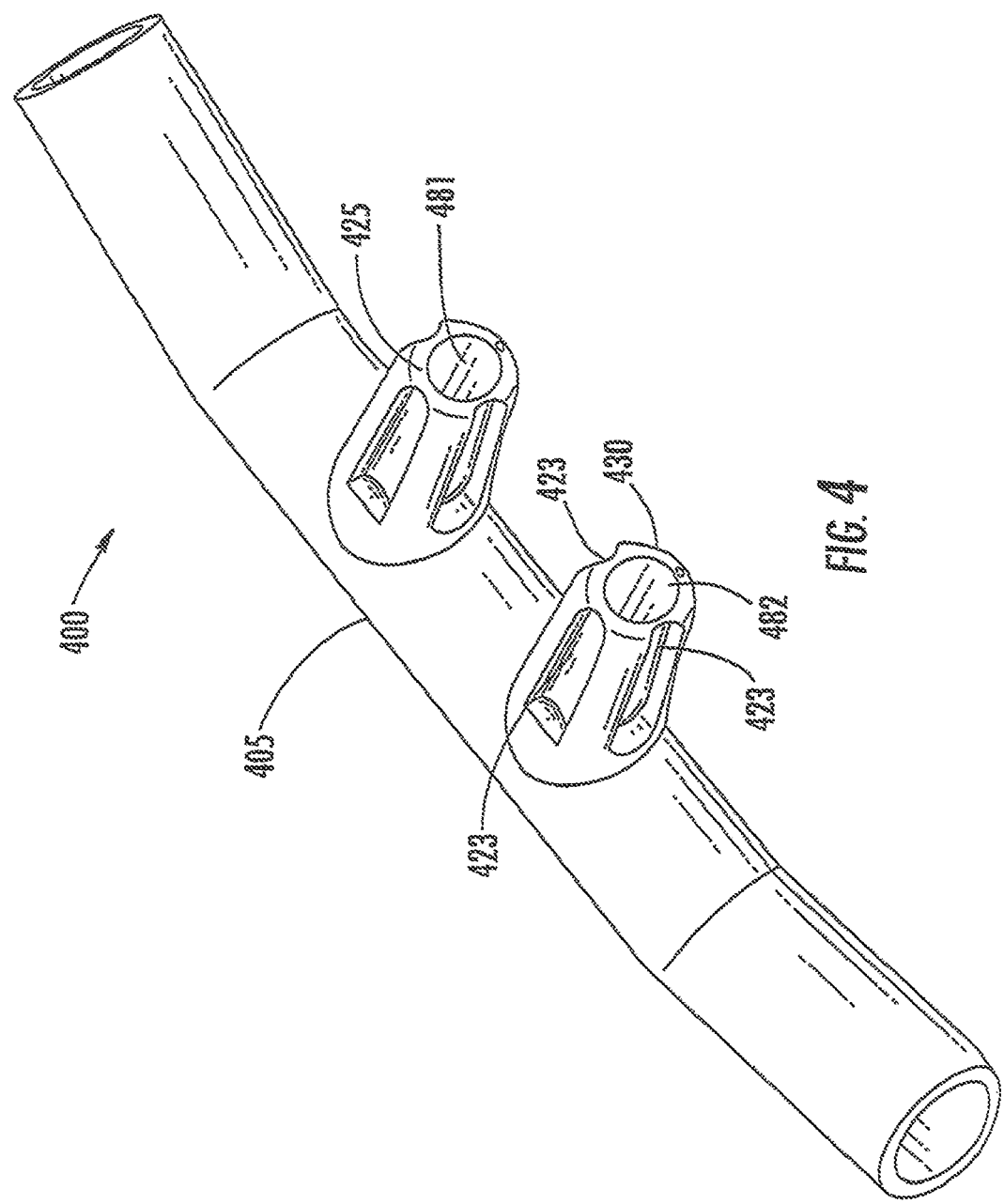
FIG. 4 is a perspective view of a nasal cannula according to yet another embodiment of the invention.

As shown in FIG. 4, in various embodiments of the invention, one or more of the nasal cannula's 400 nozzles 425, 430 includes one or more recesses 423 (e.g., grooves, semicircular recesses, or other indentations or conduits) that extend along a length of the nozzle's exterior surface. As may be understood from this figure, in various embodiments of the invention, at least one of these recesses 423 is an elongate groove that extends from adjacent a distal surface of the nozzle 425, 430 and past the midpoint between: (1) the nozzle's distal tip and (2) the portion of the nozzle 425, 430 that is immediately adjacent the nasal cannula's base portion 405. As may also be understood from this figure, in various embodiments of the invention, each groove 423 extends substantially parallel to the central axis of its respective nozzle 425, 430. Nozzles 425, 430 also have nozzle outlets 481, 482 respectively. As shown in FIG. 3, in various embodiments of the invention, one or more of the nasal cannula's 300 nozzles 325, 330 includes one or more recesses 323 that extend along a portion of length of the nozzle's exterior surface. As may be understood from this figure, in various embodiments of the invention, at least one of these recesses 323 is an elongate groove that extends from adjacent a distal surface of the nozzle 325, 330 between: (1) the nozzle's distal tip and (2) the portion of the nozzle 325, 330 that is immediately adjacent the nasal cannula's base portion 305. As may also be understood from this figure, in various embodiments of the invention, each groove 323 extends substantially parallel to the central axis of its respective nozzle 325, 330. Nozzles 325, 330 also have nozzle outlets 381, 382 respectively.

In particular embodiments of the invention, such as the embodiment shown in FIG. 4, at least one of the nasal cannula's nozzles 425, 430 is configured so that when the nozzles 425, 430 are operatively positioned within a user's nares, the nozzles do not form an airtight seal with the user's nares. This may be due, for example, to the ability of air to flow adjacent the user's rare through recesses 423 in the nozzles 425, 430 when the user is wearing the nasal cannula.

FIGS. 5-8 depict additional embodiments of the invention that are configured so that when the cannula's nasal inserts are operatively positioned adjacent (e.g., partially within) the user's nares, the nasal inserts do not form a seal with the user's nares. For example, in the embodiment shown in FIG. 5, at least one (and preferably both) of the cannula's nasal inserts 525, 530 comprise an inlet 555 (which may, for example, be substantially tubular), and one or more flange portions 560, 561 that are adapted to maintain a physical separation between an exterior side surface of the inlet 555 and a user's nare when the nasal insert 525, 530 is inserted into the user's nare.

Figure 5:
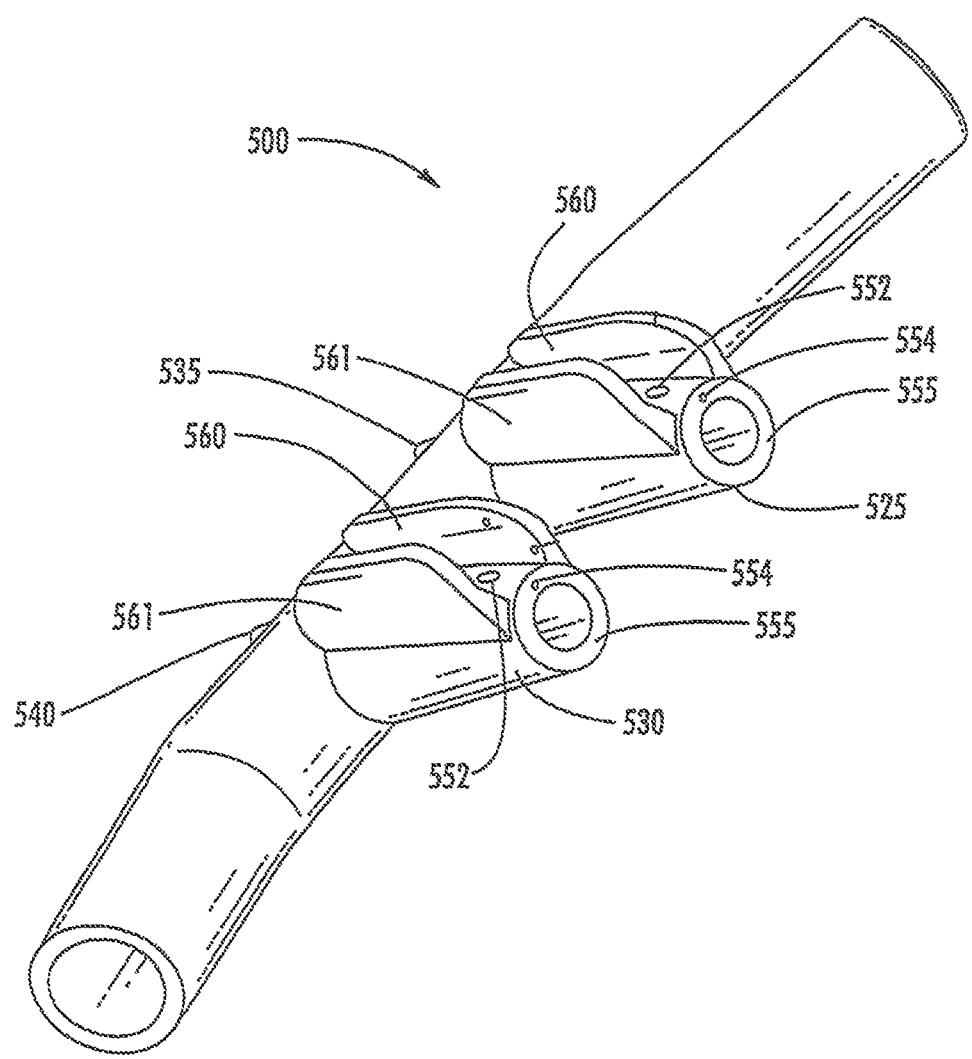
FIG. 5 is a front perspective view of a nozzle according to a further embodiment of the invention.

For example, in the embodiment of the invention shown in FIG. 5, each of the cannula's nozzles 525, 530 includes a substantially tubular nozzle body portion 555 and a pair of co-facing, elongated flanges 560, 561 that each have a substantially C-shaped cross section. In this embodiment, these C-shaped flanges 560, 561 cooperate with a portion of the exterior of the nozzle body portion 555 to form a substantially U-shaped channel (which is one example of a "nasal lumen") through which ambient air may flow to and/or from a user's nasal passages when the cannula 500 is operatively in place within the user's nares. In this embodiment, when the nozzles 525, 530 are properly in place within the user's nares, respiratory gas is free to flow into the user's nose through the nozzle body portion 555, and ambient air is free to flow into and out of the user's nose through a passage defined by: (1) the flanges 560, 561; (2) the exterior side surface of the nozzle body portion 555 that extends between the flanges 560, 561; and (3) an interior portion of the user's nose. In various embodiments, air may flow to and/or from a user's nose through this passage when the cannula 500 is operatively in place within the user's nares. A pathway (e.g., a semicircular pathway) may be provided adjacent the interior end of this U-shaped channel, which may act as a passageway for gas exhaled and inhaled through the U-shaped channel. In embodiments, nozzles 525, 530 may have conduit inlets 552, 554, and cannula 500 may have conduit outlets 535, 540.

Figure 6:
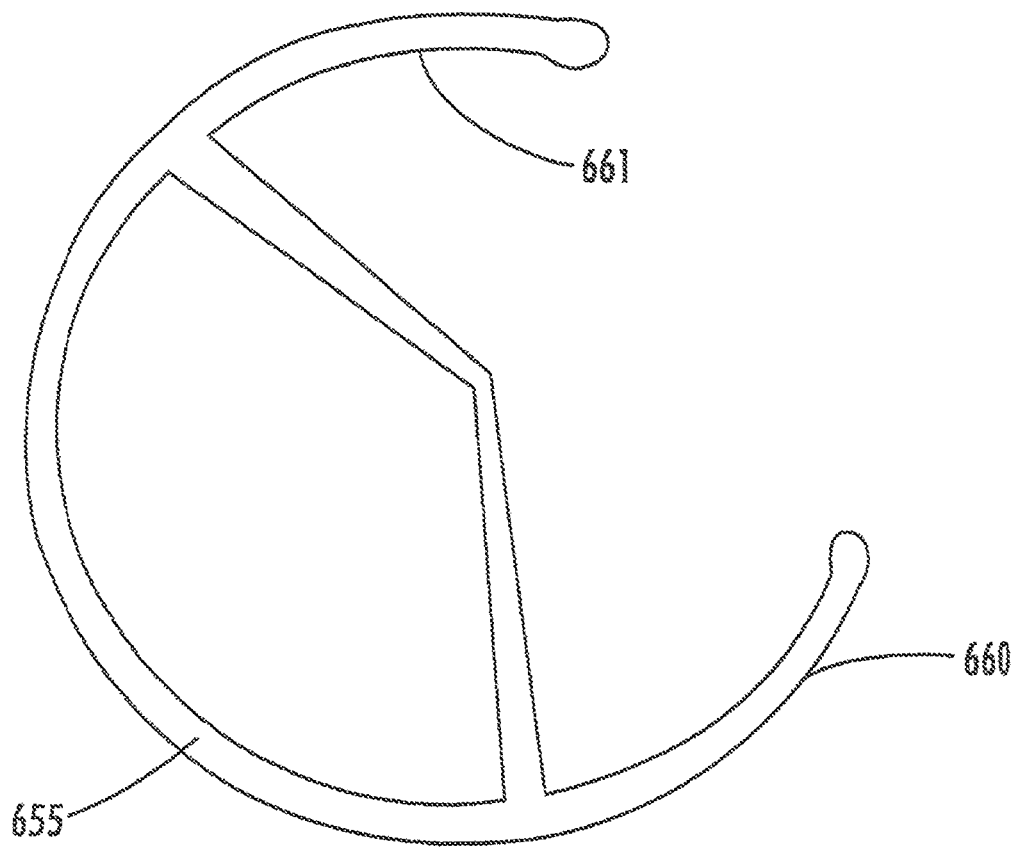
FIG. 6 depicts a cross section of a nozzle of a nasal cannula according to a particular embodiment of the invention.

The general embodiment shown in FIG. 5 may have many different structural configurations. For example, as shown in FIG. 6, which depicts a cross section of a nozzle according to a particular embodiment of the invention, the respiratory gas passageways of the cannula's nozzles 655 may be in the form of a tube having an irregular cross section (e.g., a substantially pie-piece-shaped cross section) rather than a circular cross section. Alternatively, as may be understood from FIG. 7, the respiratory gas passageways of the cannula's nozzles 755 may be in the form of a tube having a substantially half-circular cross section rather than a circular cross section.

Figure 7:
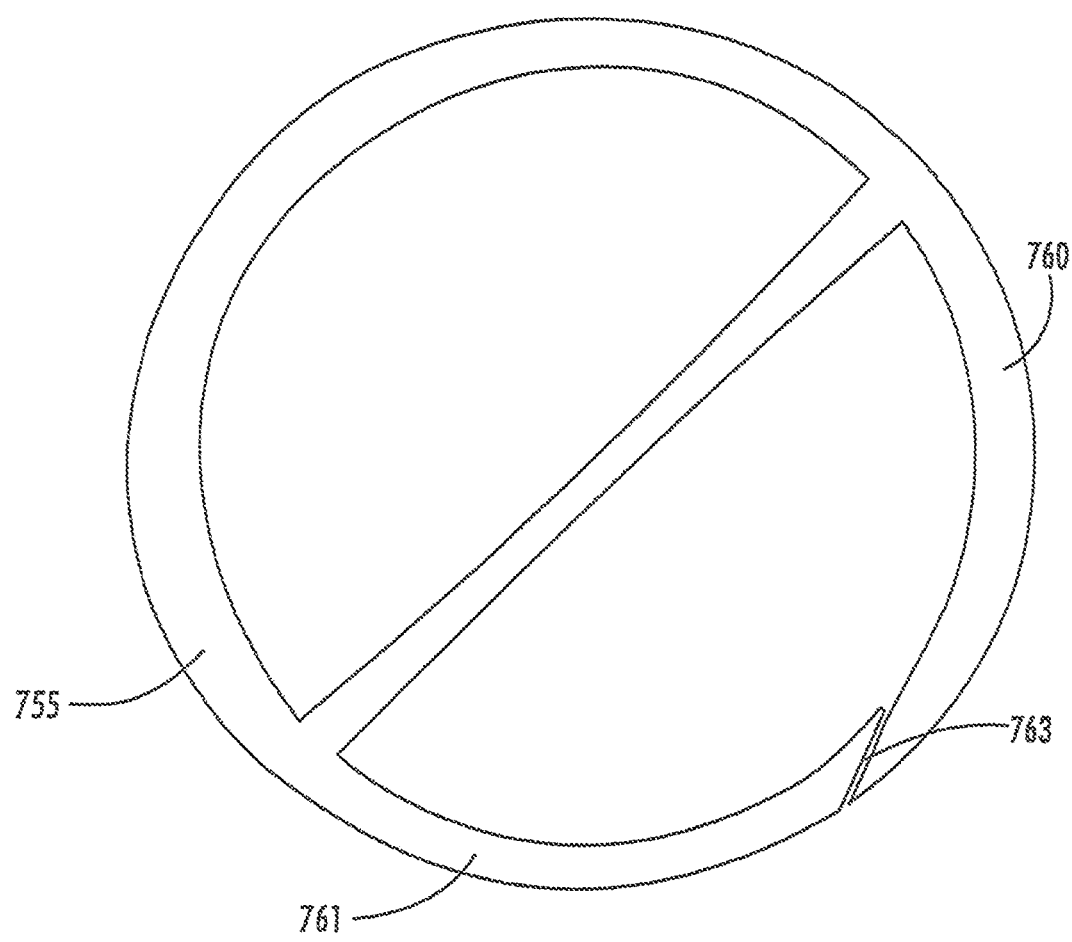
FIG. 7 depicts a cross section of a nozzle of a nasal cannula according to a further embodiment of the invention.

Similarly, as may be understood from FIGS. 6 and 7, the shape and size of the cannula's flanges may vary from embodiment to embodiment. For example, in the embodiment shown in FIG. 6, each of the flanges 660, 661 has a relatively short, substantially C-shaped cross section and the distal ends of flanges 660, 661 are spaced apart from each other to form a gap. As shown in FIG. 7, in other embodiments, each of the flanges 760, 761 may have a relatively long, substantially C-shaped cross section and the distal ends of the flanges 760, 761 may be positioned immediately adjacent each other.

As may be understood from FIG. 7, in various embodiments of the invention, a separation 763 (e.g., a slit, such as an angular slit) is provided between the flanges 760, 761. This may allow the flanges 760, 761 to move relative to each other and to thereby conform to the rare in which the nozzle is inserted. In other embodiments, the cross section of the nozzles is substantially as that shown in FIG. 7, except that no separation 763 is provided within the semi-circular flange portion. Accordingly, in this embodiment of the invention, a substantially semi-circular portion of the exterior of the air passageway cooperates with a substantially semi-circular portion of the flange portion to form an exterior having a contiguous, substantially circular cross section. One such embodiment is shown in FIGS. 8A-8C.

As may be understood from FIGS. 8A-8C, in this embodiment, when the cannula 800 is in use, respiratory gas may flow into the user's nose through inspiratory passageways 881 that extend through each of the cannula's nozzles 825, 830. Inspiratory passageways 881 are in gaseous communication with the interior of base portion 805 as shown in FIG. 8C. An expiratory passageway 885 of substantially semi-circular cross section extends between the distal end of each nozzle 825, 830 to a substantially semicircular expiratory passageway outlet 865 defined within the cannula's base portion 805. In various embodiments, when the cannula 800 is in use, the user may exhale or both inhale and exhale gas through this expiratory passageway 885. As previously mentioned, this cannula embodiment does not form a seal within the user's nares due to the expiratory passageways 885, even if the nozzles 825, 830 tightly fit within the nares. In further embodiments, nozzles 825, 830 may have recesses 823.

In certain embodiments, as discussed above, a conduit 850 is provided in each of the cannula's nozzles 825, 830 (see FIG. 8C) and may have conduit inlets 852, 854. Each of these conduits 850 may be adapted to facilitate measuring gas data by: (1) receiving gas from the interior of a corresponding expiratory passageway 885 and/or from adjacent the exterior of one of the cannula's nozzles 825, 830, and/or (2) guiding the gas out of a corresponding conduit outlet 835, 840 in the cannula 800. As discussed above, one or more sensors may be disposed within, or adjacent, the conduit 850 and used to assess one or more attributes of gas flowing through or adjacent the conduit 850.

It should be understood that the embodiments of the invention shown in FIGS. 4-8 and related embodiments may have utility with
or without the use of sensors or sensor conduits. It should also be understood that the various nozzles may be configured to be disposed in any appropriate orientation within the user's nares when the cannula is operably positioned within the user's nares. For example, in one embodiment of the invention, the cannula may be positioned so that the cannula's nasal lumen is immediately adjacent, or so that it faces anterior-laterally away from, the user's nasal spine.

Turning to yet another embodiment of the invention, as shown in FIG. 9, the cannula 900 may be adapted so that a conduit inlet 970, 972 for at least one sensor (or the sensing conduit itself) is maintained adjacent, and spaced a predetermined distance apart from, the distal end of a respective nozzle 925, 930. In this embodiment, the sensor (or conduit inlet) may be spaced apart from the rest of the nasal cannula 900 adjacent one of the nozzle outlet openings. In embodiments, cannula 900 may have conduit outlets 935, 940.

As may be understood from FIG. 10, in various embodiments, the first and second nozzles 1026, 1031 of the nasal cannula are configured to remain outside of the user's nares while the cannula is in use. For example, the nozzles may be of a length such that, when the cannula is in use, the distal ends of the nozzles 1026, 1031 lie adjacent, but outside, the user's flares. By preventing insertion of the nozzles 1026, 1031 into the nares, sealing of the nares can be avoided. As may be understood from FIG. 13, in various embodiments, when the nasal cannula is in an operative position adjacent the user's nares, an outlet portion (and distal end) of each nozzle 1326, 1331 is spaced apart from, and substantially in-line (e.g., substantially co-axial) with, a corresponding one of the patients nares. In various embodiments, when the nasal cannula is operatively in use, the outlet of each nozzle is spaced apart, from the patient's nares and each nozzle is positioned to direct a focused flow of gas into a particular respective one of the user's nares.

Referring to FIG. 11, cannula 1100 includes a hollow, elongated tubular base portion 1105 that includes a central portion 1110, a first end portion 1115, and a second end portion 1120. The first and second end portions 1115, 1120 may be angled relative to the central portion 1110, as shown in FIG. 11. In various embodiments of the invention, the cannula 1100 includes a first tubing inlet 1117 adjacent the outer end of the first end portion 1115, and a second tubing inlet 1122 adjacent the outer end of the second end portion 1020. As may be understood from FIG. 11, in particular embodiments, a stop 1190 may extend outwardly from the base portion 1105 of the nasal cannula 1100. In some embodiments, the stop 1190 lies in between the first and second nozzles 1126, 1131 and defines a central axis that runs substantially parallel to the respective central axes of the nozzles 1126, 1131. The stop 1190, in some embodiments, may extend outwardly from the nasal cannula's base portion 1105 a length greater than that of the nozzles 1126, 1131. In this manner, the stop 1190 prevents the nozzles 1126, 1131 from being inserted into the user's nares when the nasal cannula 1100 is in use.

For example, the stop 1190 may be positioned so that when the nasal cannula 1100 is in use, the stop is designed to engage the columella of the user's nose and thereby prevent the nozzles 1126, 1131 from being inserted into the user's nares. In various embodiments, the first and second nozzles 1126, 1131 are positioned on either side of the stop 1190 so that when the nasal cannula 1100 is operatively in use, the each nozzle 1126, 1131 will be spaced apart from a respective particular one of the patient's nares and will be positioned to direct a focused flow of gas into that particular rare by, for example, being positioned so that the outlet (and distal end) of each nozzle (first nozzle outlet 1183 and second nozzle outlet 1184) is substantially in-line (e.g., substantially co-axial) with, a corresponding one of the patient's nares. Similar to cannula 1000, cannula 1100 has elongate extensions 1170, 1172 that have conduit inlets at the distal ends. Elongate extensions 1170, 1172 are in gaseous communication with conduits, such as conduit 1123.

As may be understood from FIG. 12, in various embodiments, the nasal cannula 1200 may include only a single nozzle 1227. The nozzle 1227, in various embodiments, has an oblong or substantially elliptical cross-section. In these embodiments, the major axis of the ellipse runs substantially parallel to the central axis of the base portion 1205 of the nasal cannula. In one embodiment, the nozzle 1227 is wide enough to allow air to flow into both of a user's nares when the nasal cannula is in use. For example, in various embodiments, the width of the nozzle 1227 (e.g., a length defined by the major axis of the nozzle's elliptical cross section) may be approximately equal to (or greater than) the total width of the user's nares. In various embodiments, the cannula 1200 includes a first tubing inlet 1217 and a second tubing inlet 1222.

As may be understood from FIG. 14, when the nasal cannula is operatively in use, a first lateral side 1430 of the nozzle 1429 is spaced apart from, and adjacent, a user's first nare, and a second lateral side 1431 of the nozzle 1429 is spaced apart from, and adjacent, the user's second nare. In this and other configurations, the nozzle 1429 is configured to direct a focused flow of gas simultaneously into each of the user's nares. In various embodiments, when the nozzle is of a certain width, for example, approximately equal to (or greater than) the total width of the user's nares, and other widths, the nozzle 1429 is sufficiently wide to prevent the nozzle 1429 from being inserted into a user's nare, thus preventing sealing of the nasal cannula with the nare and/or is sufficiently wide to act as a stopping feature to prevent the nozzle 1429 from being inserted in the user's nares when the nasal cannula is in use. In various embodiments, first and second elongate extensions 1470, 1472 are inserted into the patient's nares. In various embodiments, the cannula has tubing 1427 which may have multiple conduits and may be positionable around the ear(s) of the user during use.

In various other embodiments, the cannula's single nozzle may have a different cross-section that is not oblong or elliptical. For example, the nozzle may have a substantially circular cross-section, with a diameter that is wide enough to allow air to flow into both of a user's nares when the cannula is in use, while simultaneously being wide enough to prevent insertion into a single nare. In various other embodiments, the nasal cannula may have more than one nozzle, each having a substantially oblong cross section and a width that prevents insertion into each of a user's nares.

In various embodiments, one or more of the cannula's elongate extensions has a diameter that is adapted to prevent sealing with the user's nares. For example, the elongate extension(s) may have a diameter that is substantially narrower than a user's nares, so that sealing is avoided, other embodiments, the elongate extension(s) may include features such as grooves or recesses, as described above, to prevent sealing when inserted into a user's nare(s). In other embodiments, the intersection of the nozzle and the extensions (or conduits) creates a recess that prevents sealing when the cannula is inserted into a user's nares.

Exemplary Use of the Cannula

To use a cannula according to a particular embodiment of the invention, a physician or technician may have a patient use the cannula for a brief period of time, while the physician or technician monitors information received from the cannula's various sensors, or the information may be recorded for later analysis. The physician or technician may then use this information to adjust the structure or operation of the cannula until the cannula's sensors indicate that the patient's upper airway environment satisfies certain conditions.

Similarly, in various embodiments, the cannula's sensors may be used to monitor conditions within the patient's upper airway over time. In a particular embodiment, the cannula's sensors may be connected to a control system that will automatically alter or modify the flow of therapeutic gas into the cannula if information from the sensor indicates undesirable conditions within the patient's upper airway. In further embodiments of the invention, the sensor is connected to a control system that issues an alarm if information from the cannula's sensors indicates undesirable conditions within the patient's airway.

Figure 13:
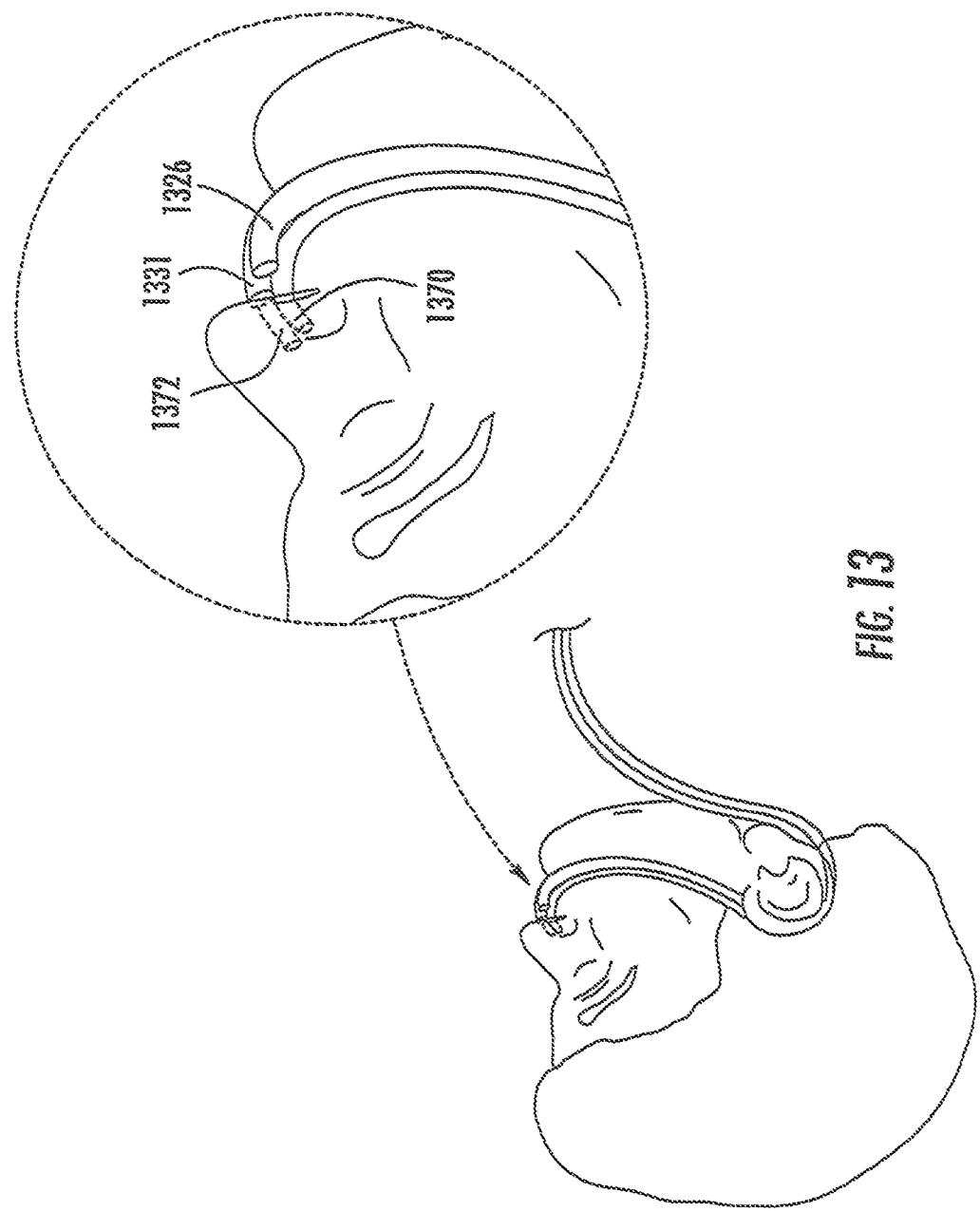
FIG. 13 illustrates an embodiment of a nasal cannula in use on a patient, according to one embodiment of the invention.

FIGS. 13 and 14 depict various embodiments of nasal cannulas being used on a patient. As may be understood from FIG. 13, for example, a nasal cannula is used on a young or small infant for high flow therapy. For example, a nasal cannula similar to that shown in FIG. 10 can be used. In various embodiments, first and second elongate extensions 1370, 1372 are inserted into the patient's nares, while corresponding first and second nozzles 1326, 1331 remain adjacent and external to the patient's nares. As may be appreciated, when the nasal cannula is in use, air flows into the patient's nares via the nozzles. FIG. 14 depicts one embodiment of a nasal cannula in use on a patient. In one embodiment, a nasal cannula such as that shown in FIG. 12 can be used. As may be understood from FIG. 14, a nasal cannula having a single nozzle 1429 can be used, in which the nozzle is sized and shaped (e.g., is elliptical and/or wider than a patient's nare) to prevent insertion into the patient's nares. In various other embodiments, nasal cannula having nasal insert type nozzles, as described throughout, can be used. In these embodiments, the nasal inserts are inserted into the user's nares while the cannula is in use. Nasal cannula according to embodiments of the invention can be used on a variety of patients.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. For example, although the embodiment shown in FIG. 1 shows each nozzle 125, 130 having two conduit inlets 152, 154, in alternative embodiments of the invention, one or more of the nozzles 125, 130 may have more or less than two conduit inlets (and/or more or less than two sensors). Although specific terms are employed herein, they are used in a generic and descriptive sense only and not for purposes of limitation.

What is claimed is:

1. A nasal cannula comprising:
a base portion defining a first therapeutic gas passageway that is configured to receive pressurized gas to deliver respiratory therapy to a patient;
a nasal insert disposed adjacent said base portion and defining a second therapeutic gas passageway, the nasal insert being configured to be at least partially inserted into the patient's nare to provide high flow respiratory therapy, said second therapeutic gas passageway being in gaseous communication with and extending from said first therapeutic gas passageway so as to receive the pressurized gas from the first therapeutic gas passageway and to deliver the pressurized gas through the second therapeutic passageway into the patient's nare when the nasal insert is inserted at least partially into the patient's nare, wherein an external surface of the nasal insert includes one or more features that are configured to prevent the nasal insert from forming a seal with the patient's nare when providing the high flow respiratory therapy; and
at least one sensor for measuring the properties of gas adjacent said nasal insert,
wherein the one or more features included on the external surface of the nasal insert comprises one or more recesses formed in the external surface of the nasal insert,
wherein the at least one sensor is positioned within the one or more recesses of the nasal insert and is connected to at least one electrical wire that extends from the at least one sensor and from nasal insert, wherein the at least one sensor is configured to transmit an signal via the electrical wire that indicates the measured properties of the gas adjacent to the nasal insert.

2. The nasal cannula of claim 1, wherein the nasal insert includes a first end attached to the base portion and a second distal end that is inserted into the patient's nare and that defines an opening through which pressurized respiratory gas is delivered to the patient as part of the high flow respiratory therapy.

3. The nasal cannula of claim 2, wherein the one or more recesses extend along only a portion of a length of the nasal insert from the first end to the second distal end.

4. The nasal cannula of claim 3, wherein the one or more recesses extend to the second distal end.

5. The nasal cannula of claim 2, wherein the one or more recesses extend along a length of the nasal insert from the first end to the second distal end.

6. The nasal cannula of claim 1, wherein the one or more recesses comprise one or more grooves defined in the external surface of the nasal insert.

7. The nasal cannula of claim 6, wherein the one or more grooves extend substantially parallel to a central axis of the nasal insert.

8. The nasal cannula of claim 1, wherein the one or more recesses have a semicircular shape.

9. The nasal cannula of claim 1, wherein the one or more recesses comprise one or more indentations in the external surface of the nasal insert.

10. The nasal cannula of claim 1, wherein the one or more features included on the external surface of the nasal insert further comprises one or more structures extending from the external surface of the nasal insert that are configured to maintain physical separation between the patient's nare and at least a portion of the external surface of the nasal insert.

11. The nasal cannula of claim 10, wherein the one or more structures comprise one or more flanges extending from the nasal insert.

12. The nasal cannula of claim 11, wherein the one or more flanges comprise a pair of co-facing flanges.

13. The nasal cannula of claim 12, wherein the pair of co-facing flanges have a C-shaped cross-section.

14. The nasal cannula of claim 11, wherein the nasal insert has a circular cross section from with the one or more flanges extend.

15. The nasal cannula of claim 11, wherein the nasal insert has an irregularly shaped cross section from which the one or more flanges extend.

16. The nasal cannula of claim 15, wherein the one or more flanges have a C-shaped cross section with a curvature corresponding to a curved portion of the nasal insert's external surface.

17. The nasal insert of claim 16, wherein a distal end of the C-shaped cross section of the one or more flanges defines a gap along the curvature.

18. The nasal cannula of claim 16, wherein distal ends of the C-shaped cross sections of the one or more flanges are adjacent each other.

19. The nasal cannula of claim 1, wherein the least one sensor is configured to be detachable from a position adjacent the nasal insert.

20. The nasal cannula of claim 19, wherein the position adjacent the nasal insert comprises a portion of the nasal insert.

* * * * *